US00PP15597P3

(12) United States Plant Patent
Ackerman et al.

(10) Patent No.: US PP15,597 P3
(45) Date of Patent: Mar. 1, 2005

(54) STRAWBERRY PLANT NAMED PS-2880

(50) Latin Name: *Fragaria ananassa*
Varietal Denomination: PS-2880

(76) Inventors: Stephen M. Ackerman, 261 Alhambra St., Salinas, CA (US) 93906; Michael D. Nelson, 136 Litchfield Ln, Watsonville, CA (US) 95076; Steven D. Nelson, 120 Litchfield Ln, Watsonville, CA (US) 95076

( * ) Notice: Subject to any disclaimer, the term of this patent is extended or adjusted under 35 U.S.C. 154(b) by 142 days.

(21) Appl. No.: 10/678,063

(22) Filed: Oct. 6, 2003

(65) Prior Publication Data

US 2004/0073979 P1 Apr. 15, 2004

Related U.S. Application Data

(60) Provisional application No. 60/418,237, filed on Oct. 15, 2002.

(51) Int. Cl.[7] ..... A01H 5/00
(52) U.S. Cl. ..... Plt./209
(58) Field of Search ..... Plt./209

*Primary Examiner*—Bruce R. Campell
*Assistant Examiner*—Michelle Kizilkaya

(57) ABSTRACT

This invention relates to a new and distinct day-neutral variety of strawberry plant named PS-2880. This new variety is primarily adapted to the growing conditions of the central coast of California. The new variety is primarily characterized by its medium to large sized plant, many crowns per plant, low frequency of small to very small bract leaflets on the petioles, long petiolules, large diameter stolons, strong stolon pubescence, high number of sepals per berry, conical to wedged shaped fruit, absent to very narrow band without achenes on the fruit, achenes set more consistently above the fruit, spreading to reflexed calyx segments, calyx which is weakly attached to the fruit and strongly expressed hollow center.

5 Drawing Sheets

Genus and species of the plant claimed: *Fragaria ananassa.*
Variety denomination:'PS-2880'.

BACKGROUND OF THE INVENTION

This application is based on U.S. provisional plant patent application Ser. No. 60/418,237, filed Oct. 15, 2002.

The present invention relates to a new and distinct day-neutral strawberry variety designated as 'PS-2880'. This new variety is a result of a controlled cross made in 1992 between 'PS-592' (U.S. Plant Pat. No. 9,903) and 'PS-1391' (an unpatented Plant Sciences, Inc. selection). The new variety is botanically known as *Fragaria ananassa.*

The seedling resulting from the aforementioned cross was asexually propagated by stolons in a nursery located in Lassen County, Calif. The Seedling was then subsequently selected from a controlled breeding plot in Salinas, Calif. in 1994. After its selection, the new variety was further asexually propagated by stolons in Lassen County, Calif., Modoc County, Calif., Siskiyou County, Calif. and San Joaquin County, Calif. The new variety was then extensively tested over the next several years in the fruiting fields of Salinas, Calif. This propagation has demonstrated that the combination of traits disclosed herein as characterizing the new variety are fixed and remain true to type through successive generations of asexual reproduction.

BRIEF SUMMARY OF THE INVENTION

'PS-2880' is primarily adapted to the climate and growing conditions of the central coast of California. This region provides the necessary winter temperatures required for it to produce a strong vigorous plant and to remain in fruit production from April through November. The nearby Pacific Ocean provides the needed humidity and moderate temperatures to maintain fruit quality during the spring and summer production months.

The varieties which are believed to be most closely related to 'PS-2880' are 'PS-592' and 'PS-1150' (U.S. Plant Pat. No. 10,780).

In comparison to the similar variety, 'PS-592', 'PS-2880' differs by the following combination of characteristics. 'PS-2880' type of bearing is day-neutral as compared to 'PS-592' which is fully remontant. The plant of 'PS-2880' is smaller in size, less vigorous, with more crowns per plant than 'PS-592'. The foliage is smaller in size, serrations are more abundant yet shallower than 'PS-592'. Bract leaflets occur much less frequent on the petioles. Petiole pubescence and petiolule lengths are both greater as compared to 'PS-592'. The average fruit size of 'PS-2880' is smaller with a conical to wedged shaped berry as compared to 'PS-592' which tends to be more conical and larger in size. The calyx tends to be slightly smaller in diameter with more sepals per berry as compared to 'PS-592'. 'PS-2880' skin and flesh color is a darker red than 'PS-592'. Achenes are set much more above the surface of the berry than 'PS-592'. Adherence of the calyx is much more weakly attached to the berry as compared to 'PS-592'. The fruiting trusses of 'PS-2880' are shorter in length with much stronger anthocyanins as compared to 'PS-592'.

In comparison to the similar variety, 'PS-1150', 'PS-2880' differs by the following combination of characteristics. 'PS-2880' type of bearing is day-neutral as compared to 'PS-1150' which is fully remontant. The plant of 'PS-2880' is larger in size, more vigorous, with more crowns per plant than 'PS-1150'. The stolons of 'PS-2880' are larger in diameter with less anthocyanins than 'PS-1150'. The foliage is larger in size, more consistently concave in cross section with much stronger interveinal leaf blistering than 'PS-1150'. Serrations are more abundant and deeper than those of 'PS-1150'. Bract leaflets occur less frequent on the petioles and are slightly smaller in size. Petiole pubescence and petiolule lengths are both greater as compared to 'PS-1150'. Stipules are longer in length with stronger anthocyanin colorations as compared to 'PS-1150'. The average fruit size of 'PS-2880' is larger with a conical to wedged shaped berry as compared to 'PS-1150' which tends to be more conical and smaller in size. Achenes are set much more above the surface of the berry than 'PS-1150'. Adherence of the calyx is much more weakly attached to the berry and more reflexed as compared to 'PS-1150'. The fruiting trusses of 'PS-2880' are longer in length and much less visible above the plant as compared to 'PS-1150'.

For identification a series of molecular markers have been determined for this new variety.

BRIEF DESCRIPTIONS OF THE DRAWINGS

The accompanying color photographs show typical specimens of the new variety at various stages of development as nearly true as it is possible to make in color reproductions. The depicted plant and plant parts were approximately 7 to 8 months old:

DETAILED BOTANICAL DESCRIPTION

Figure 1:
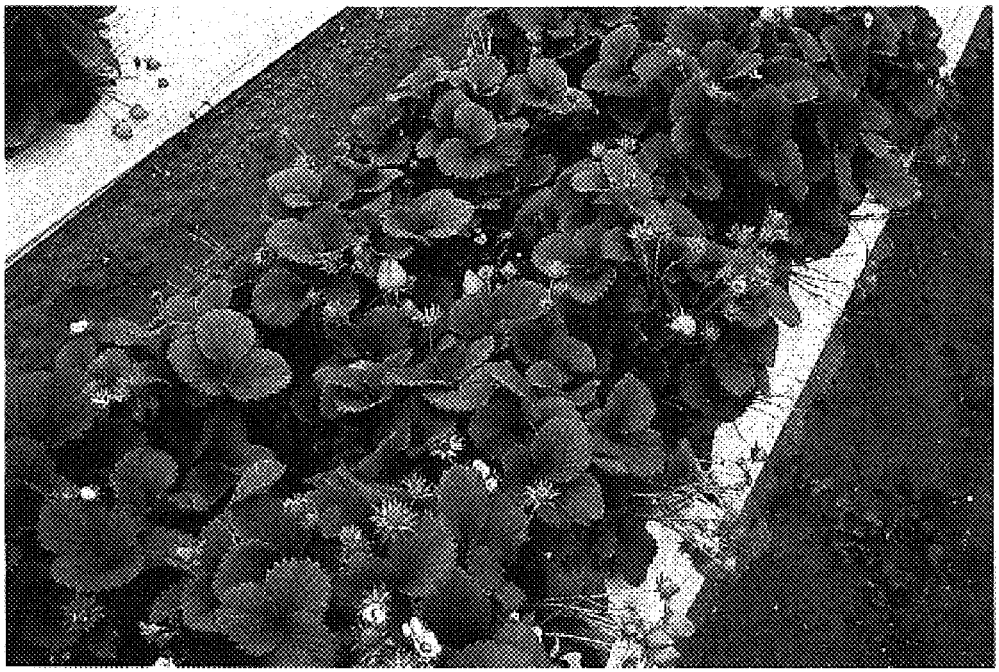
FIG. 1 shows typical fruiting field characteristics on Jul. 5, 2002.
Figure 2:
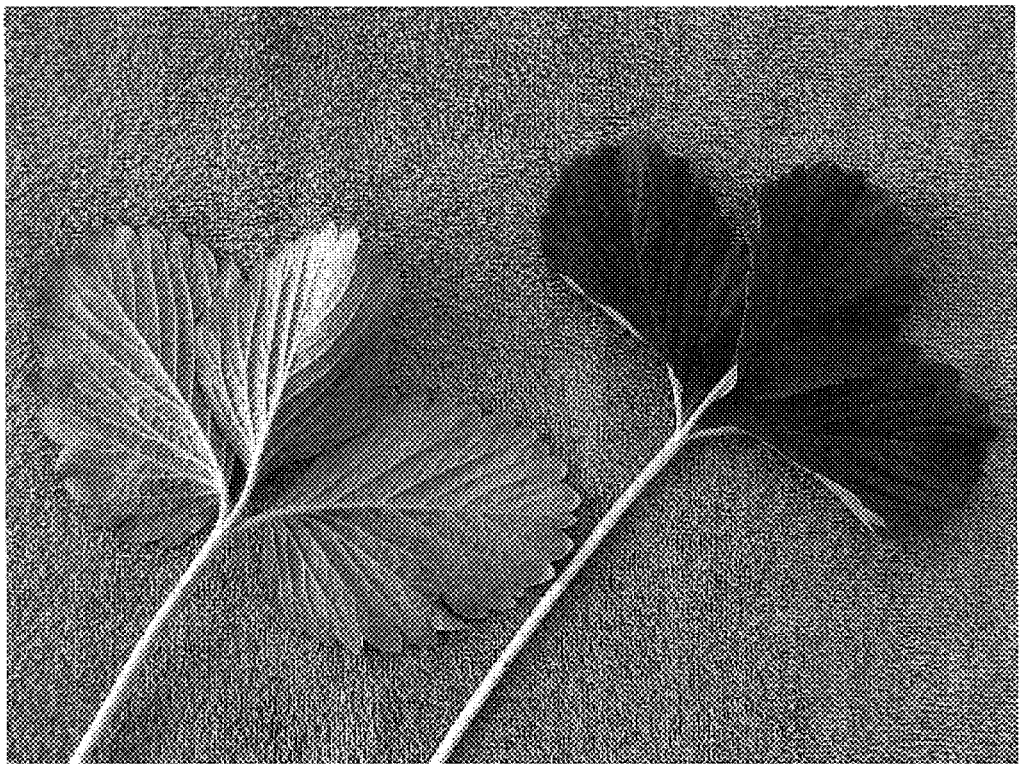
FIG. 2 shows a close-up view of a typical mature trifoliate on Jul. 11, 2003.
Figure 3:
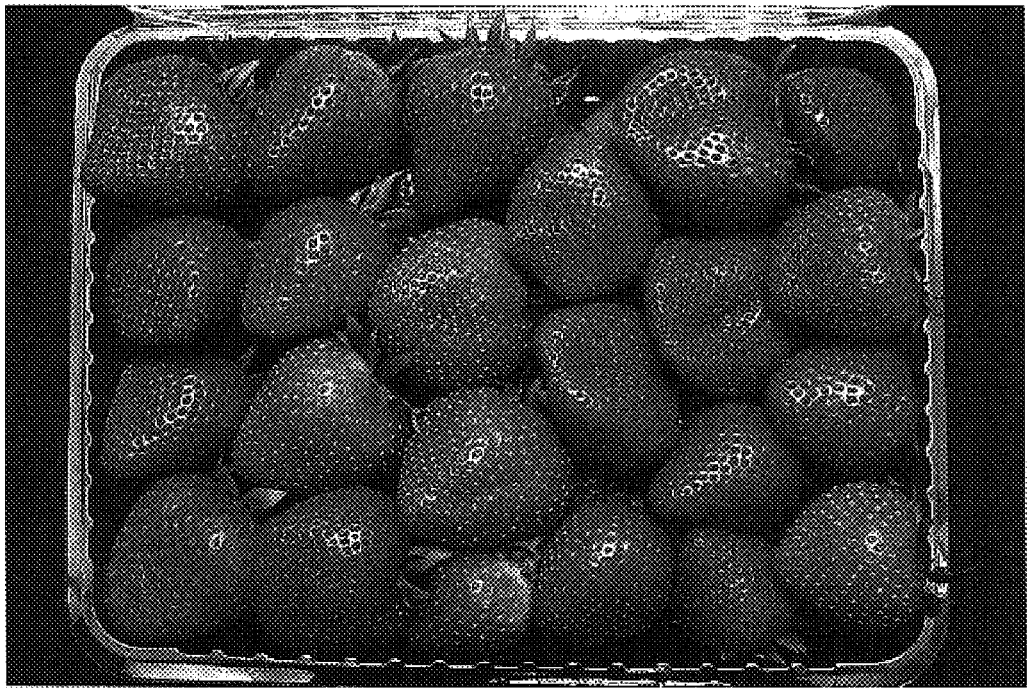
FIG. 3 shows a close-up view of fruit on Jul. 3, 2002.
Figure 4:
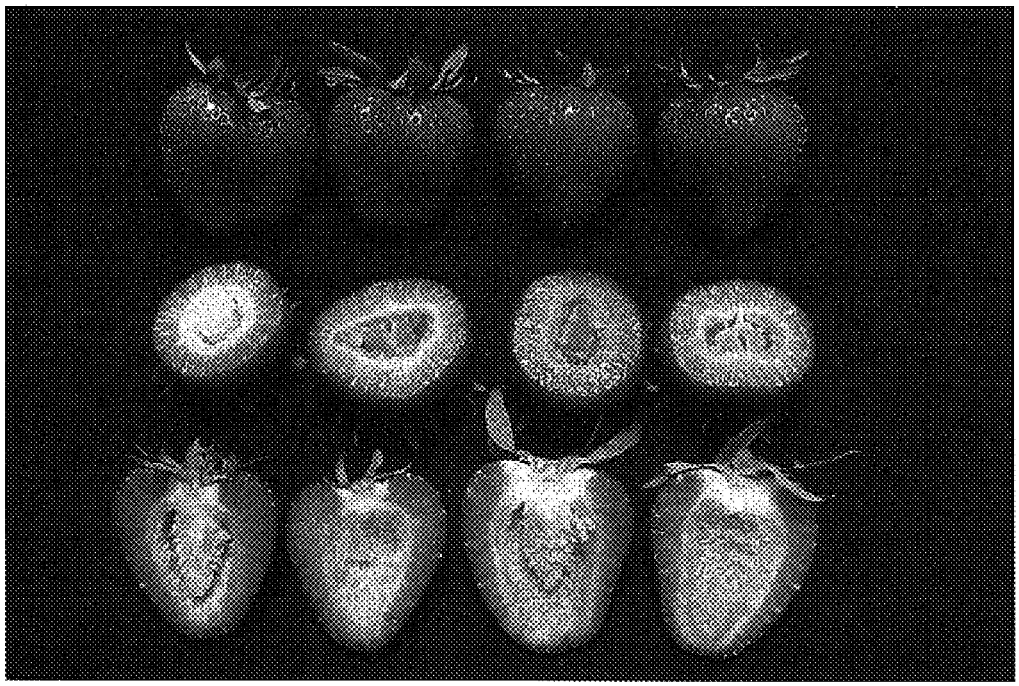
FIG. 4 shows typical internal and external fruit characteristics on Jul. 3, 2002.
Figure 5:
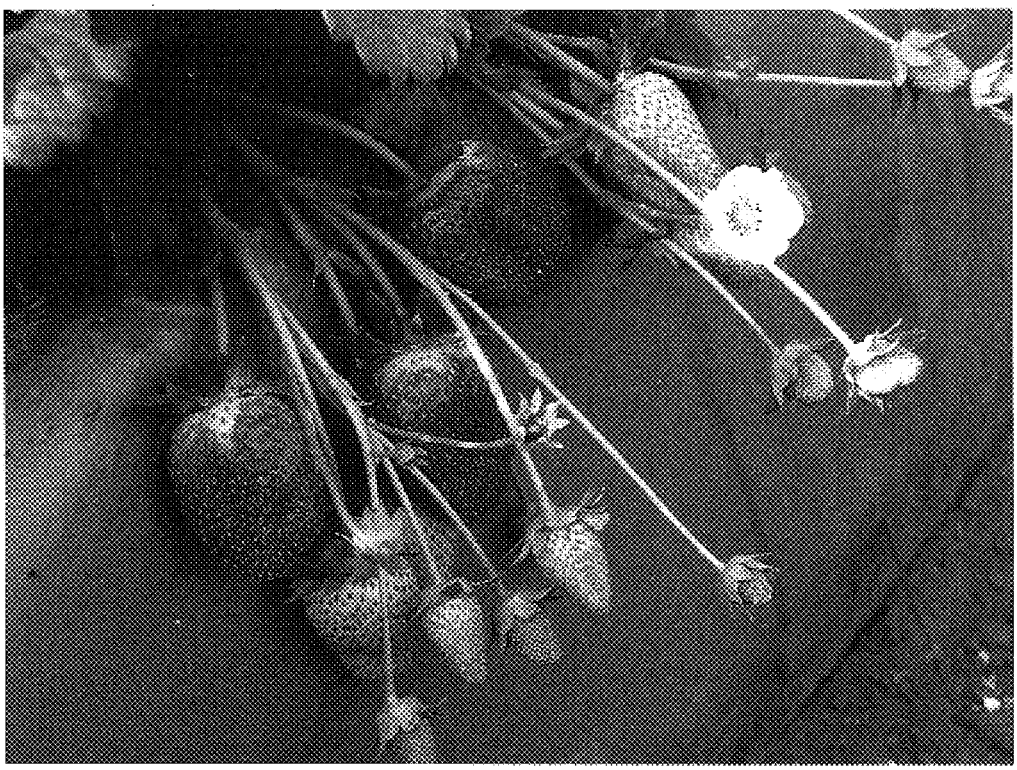
FIG. 5 shows typical mature and immature field fruit on Oct. 23, 2002.

The following description of 'PS-2880' unless otherwise noted, is based on observations taken during the 2003 growing season in Salinas, Calif. These measurements and ratings were taken from plants dug from a high-elevation nursery located in Siskiyou County, Calif. during the middle of October 2002 and planted approximately 3 weeks later in Salinas, Calif. The approximate age of the observed plants is 7 to 8 months. Yield observations and fruit quality characteristics are averaged from data collected during the 2003 production season. The characteristics of the new variety may vary in detail, depending upon variations in environmental factors, including weather (temperature, humidity and light intensity), day length, soil type and location. 'PS-2880' has not been observed under all possible environmental conditions. Color terminology where noted follows the Munsell Book of Colors, Munsell Color, Baltimore, Md. (1976).

Fruit Characteristics

'PS-2880' fruit, fruit production and fruit quality characteristics. Fruit characteristics are taken from secondary fruit on a first year planting.

TABLE 1

2003 market fruit yield, fruit size and runner production characteristics of 'PS-2880' with standards from Salinas, California.

| Cultivar | 2003 Average April/May Yield GM/PL | 2003 Average Total Yield GM/PL | 2003 Average Fruit Size GRM | 2003 Average Runners/PL |
|---|---|---|---|---|
| 'PS-2880' | 284 | 1,068 | 21.4 | 0.05 |
| 'PS-592' | 306 | 1,259 | 23.2 | 0 |
| 'PS-1150' | 192 | 1,029 | 17.5 | 0.2 |

Fruit was harvested from April through August 2003. The plants of 'PS-2880' were dug from a high elevation nursery (Macdoel, California) during the middle of October and planted approximately 3 to 4 weeks later in Salinas, California. 'PS-2880' is compared with standards dug and planted comparably.

TABLE 2

Comparison of secondary fruit characteristics of 'PS-2880', with standards from Salinas, California, Jun. 21, 2003.

| | Character | | |
|---|---|---|---|
| | 'PS-2880 | 'PS-592' | 'PS-1150 |
| Munsell Color Range Mature Fruit | 7.5R 4/8 to 3/8 | 7.5R 3/12 to 4/12 | 7.5R 3/10 to 4/10 |
| Fruit Length mean (cm) | 3.96 | 4.25 | 3.81 |
| Fruit Width mean (cm)* | 3.76 | 4.14 | 3.68 |
| Fruit Length/ Width Ratio | 1.05 | 1.03 | 1.03 |
| Calyx Diameter mean (cm) | 4.6 | 5.1 | 4.6 |
| No. Sepals/Berry | 14.7 | 13.0 | 13.5 |
| Seed Weight mean (mgs) | 0.57 | 0.52 | 0.42 |

*Width is measured across the widest part of the berry, typically across the shoulders

TABLE 3

Comparison of 2003 fruit quality characteristics, including flavor and soluble solids of 'PS-2880', with standards from Salinas, California; August 2003.

| | Character | | |
|---|---|---|---|
| | 'PS-2880' | 'PS-592' | 'PS-1150' |
| Skin Firmness* | 8.0 | 7.9 | 8.5 |
| Fruit Appearance* | 7.2 | 8.0 | 8.3 |
| Fruit Gloss* | 8.1 | 8.2 | 8.5 |
| Flavor** | 2.3 | 3.3 | 2.4 |
| Soluble Solids*** | 9.3 | 9.1 | 7.6 |

*Results are averaged from 1 year of replicated holding test performed from April through September 2003. Ratings are based on a scale from 1–10; the higher the rating, the stronger the skin and more attractive and glossy the berry.

**Results are averaged from tests performed from May through September 2003. Ratings are based on a scale from 1–5; the higher the rating the better the flavor.

***Results are averaged from tests performed from May through September 2003. Soluble solid content is measured in percent Brix, with percent Brix being an indirect measurement of the sugar content in the fruit.

Fruit:

*Ratio of length/width.*—As long as broad to slightly longer than broad.
*Size.*—Medium.
*Predominant shape.*—Conical to cordiform, occasionally wedged.
*Difference in shapes between primary and secondary fruit.*—Moderate.
*Band without achenes.*—Absent or very narrow.
*Unevenness of surface.*—Medium to strong.
*Color of mature fruit.*—Medium red.
*Evenness of color.*—Slightly uneven to even.
*Glossiness.*—Medium to strong.
*Insertion of achenes.*—Above the surface.
*Insertion of calyx.*—Level with the surface to in the basin.
*Attitude of the calyx segments.*—Spreading to reflexed.
*Size of calyx in relation to fruit diameter.*—Slightly larger.
*Adherence of calyx* (*when fully ripe*).—Weak.
*Firmness of skin.*—Medium.
*Firmness of flesh.*—Firm.
*Color of flesh.*—Medium to dark red (7.5R 3/12 to 4/12).
*Distribution of red color of the flesh.*—Marginal and central.
*Hollow center.*—Strongly expressed.
*Receptacle color.*—Whitish (N 9.25/84.2% R to N 9/78.7% R).
*Seed color.*—Medium yellow to medium red (5Y 6/8 to 7.5R 3/8).
*Time of flowering* (*50% of plants at first flower*).—Medium to early.
*Time of ripening* (*50% of plants with first ripe first*).—Medium to early.
*Time of ripening* (*length of time from flower to maturity*).—20.9 days in mid summer.
*Type of bearing.*—Day neutral.

Plant Characteristics

'PS-2880' foliage characteristics. Plant characteristics are taken from a fully mature mid season plant.

TABLE 4

Comparison of plant characteristics of 'PS-2880', with standards from Salinas, California, Jul. 11, 2003.

| | Character | | |
|---|---|---|---|
| | 'PS-2880' | 'PS-592' | 'PS-1150' |
| Plant Height mean (cm) | 27.3 | 29.2 | 23.0 |
| Plant Spread mean (cm) | 30.9 | 31.2 | 26.9 |
| Crowns/Plant (mean) | 5.1 | 4.4 | 3.8 |
| Stolon Thickness mean (mm) | 4.0 | 4.1 | 3.4 |

Plant:

*Size.*—Medium to large.
*Habit.*—Globose.
*Density.*—Medium.
*Vigor.*—Medium to strong.

Stolons:

*Number.*—Few.
*Anthocyanin coloration.*—Medium.
*Thickness.*—Thick.
*Pubescence.*—Strong.

Foliage Characteristics

'PS-2880' foliage characteristics. Foliage characteristics are taken from a fully mature tri-foliate during mid season.

TABLE 5

Comparison of leaf characteristics of 'PS-2880', with standards from Salinas, California, Jun. 6, 2003.

| | Character | | |
|---|---|---|---|
| | 'PS-2880' | 'PS-592' | 'PS-1150' |
| Munsell Color Range (upper surface) | 7.5GY 3/4 to 4/4 | 7.5GY 4/4 to 3/4 | 7.5GY 4/4 to 3/4 |
| Terminal Leaflet Length mean (cm) | 8.2 | 9.4 | 6.8 |
| Terminal Leaflet Width mean (cm) | 7.0 | 8.0 | 5.9 |
| Terminal Leaflet ratio (L/W) | 1.2 | 1.2 | 1.1 |
| Petiole Length mean (cm) | 17.4 | 19.6 | 15.2 |
| Petiole Width mean (mm) | 4.0 | 4.5 | 3.2 |
| Petiolule Length mean (mm) | 11.6 | 8.2 | 6.3 |
| Serrations/Leaf | 22.4 | 18.8 | 19.7 |
| Serration Depth mean (mm) | 5.4 | 6.1 | 4.6 |
| Stipule Length mean (cm) | 2.0 | 2.2 | 1.6 |
| Stipule Width mean (cm) | 0.9 | 1.0 | 0.8 |

Foliage:

*Color of upper surface.*—Medium to light green.
*Color of under side.*—Light grey green (5GY 5/4 to 6/4).
*Shape in cross section.*—Slightly concave.
*Blistering.*—Medium to strong.
*Glossiness.*—Medium to strong.
*Number of leaflets/leaf.*—Three.

Terminal leaflet:

*Size.*—Medium.
*Length/width ratio.*—Longer than broad to much longer than broad.
*Shape of base.*—Acute.
*Shape of incision of margins.*—Obtuse.
*Depth of serrations.*—Medium.

Petiole:

*Pubescence.*—Moderate.
*Stipule color.*—Light to medium green.
*Anthocyanin coloration of stipule.*—Medium.
*Attitude of hairs.*—Slightly outward.
*Size of bract leaflets.*—Small to very small.
*Frequency of bract leaflets.*—Few to none (occur on approx. 5% of the petioles).

Flowers and Inflorescences

'PS-2880' inflorescence and flower characteristics. Inflorescence and flower characteristic are taken from a fully mature plant during mid season.

TABLE 6

Comparison of inflorescence and secondary flower characteristics of 'PS-2880', with standards from Salinas, California, Jun. 6, 2003.

| | Character | | |
|---|---|---|---|
| | 'PS-2880' | 'PS-592' | 'PS-1150' |
| Fruiting Truss Length* mean (cm) | 30.7 | 33.1 | 27.8 |
| Corolla Diameter mean (cm) | 3.5 | 3.5 | 3.4 |
| Calyx Diameter mean (cm) | 3.7 | 4.2 | 3.6 |
| Petal Length mean (cm) | 1.4 | 1.4 | 1.5 |
| Petal Width mean (cm) | 1.4 | 1.4 | 1.4 |
| Petal L/W Ratio | 1.0 | 1.0 | 1.1 |
| Petals/Flower (mean) | 6.8 | 6.6 | 7.0 |
| Sepal Length mean (cm) | 1.4 | 1.6 | 1.4 |
| Sepal Width mean (cm) | 0.4 | 0.5 | 0.5 |
| Sepal L/W Ratio | 3.4 | 3.1 | 2.8 |
| Sepals/Flower (mean) | 13.8 | 11.5 | 11.5 |
| Stamens/Flower (mean) | 29.3 | 25.8 | 27.9 |
| Pistils/Flower (mean) | 832 | 624 | 553 |

*as measured from the base of the primary peduncle where is attaches to the crown of the plant to the furthest berry.

Inflorescence:

*Position relative to foliage.*—Level with.

*Pubescence.*—Medium.

*Anthocyanins.*—Moderate to strong.

*Number of bract leaflets per truss* (*Avg*).—1.

*Size of bract leaflets.*—Medium to small.

*Fruiting truss length.*—Medium to long.

Flowers:

*Color.*—White.

*Size.*—Medium to large.

*Size of calyx relative to corolla.*—Larger to same size.

*Relative position of.*—Overlapping.

*Petal length/width ratio.*—As long as broad.

Pest Reactions

This new variety may not be resistant to any of the known insects, diseases or viruses common in California. It is known to be moderately susceptible to the two-spotted spider mite, aphid and flower thrips. It is also known to be moderately susceptible to grey fruit mold, angular leaf spot and susceptible to powdery mildew. The susceptibility of the new variety to any of the virus complexes of California has not been determined.

We claim:

1. A new and distinct strawberry plant named 'PS-2880', as herein described and illustrated by the characteristics set forth above.

* * * * *